(12) United States Patent
Maltz et al.

(10) Patent No.: US 7,697,662 B2
(45) Date of Patent: Apr. 13, 2010

(54) ONLINE VERIFICATION OF RADIATION FIELD, COLLIMATOR POSITION AND/OR LEAKAGE

(75) Inventors: Jonathan S. Maltz, Oakland, CA (US); Dimitre Hristov Hristov, Stanford, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 87 days.

(21) Appl. No.: 11/900,433

(22) Filed: Sep. 11, 2007

(65) Prior Publication Data

US 2009/0067576 A1    Mar. 12, 2009

(51) Int. Cl.
*A61N 5/10* (2006.01)
*G21K 1/02* (2006.01)

(52) U.S. Cl. .......................................... 378/65; 378/147
(58) Field of Classification Search ................... 378/62, 378/64, 65, 207, 108, 164, 206, 147–153
See application file for complete search history.

(56) References Cited

U.S. PATENT DOCUMENTS

| | | | | |
|---|---|---|---|---|
| 6,128,366 A | * | 10/2000 | Siochi | 378/65 |
| 6,760,402 B2 | * | 7/2004 | Ghelmansarai | 378/65 |
| 7,298,820 B2 | * | 11/2007 | Nelson | 378/65 |

\* cited by examiner

*Primary Examiner*—Irakli Kiknadze

(57) ABSTRACT

A system includes delivery of treatment radiation to a target, acquisition of an image representing the treatment radiation during delivery of the treatment radiation, determination of a position of a leaf of a collimator delivery of the treatment radiation based on the image, and presentation of a notification of an error during delivery of the treatment radiation based on the determined position.

18 Claims, 11 Drawing Sheets

ONLINE VERIFICATION OF RADIATION FIELD, COLLIMATOR POSITION AND/OR LEAKAGE

BACKGROUND

1. Field

The embodiments described below relate generally to the delivery of therapeutic radiation to a patient. More specifically, some embodiments are directed to treatment verification systems used in conjunction with such delivery.

2. Description

According to conventional radiation treatment, a radiation beam is directed toward a tumor located within a patient. The radiation beam delivers a predetermined dose of therapeutic radiation to the tumor according to a pre-established treatment plan. The delivered radiation kills cells of the tumor by causing ionizations within the cells.

Radiation treatment plans are designed to maximize radiation delivered to a target while minimizing radiation delivered to healthy tissue. These goals might not be achieved if the radiation is not delivered exactly as required by the treatment plan. More specifically, errors in radiation delivery can result in low irradiation of tumors and high irradiation of sensitive healthy tissue. The potential for mis-irradiation increases with increased delivery errors.

Delivery errors may arise from many sources. For example, a patient position may vary from that required by a treatment plan, internal patient anatomy may be displaced with respect to external visible markers, and/or characteristics (e.g., flatness, symmetry and penumbra) of the delivered radiation beam may not match beam characteristics on which the treatment plan is based. Devices used to shape the radiation beam may provide another potential source of errors.

Generally, incorrect positioning of beam-shaping devices may result in a radiation field that is not shaped as required by a treatment plan. For example, a treatment plan may specify a degree of rotation for a multi-leaf collimator used to shape a radiation beam, and may also specify particular positions for each jaw and leaf contained therein. Any deviance between the actual rotation/positions and the specified rotation/position may result in delivery errors. Unexpected radiation leakage around or between the jaws/leaves may also result in errors.

Quality assurance procedures are typically performed periodically and/or prior to radiation treatment in order to detect and correct potential radiation delivery errors. These procedures are particularly time-consuming and often inefficient. Delivery errors may also be identified after treatment, in which case a next fraction may be modified in an attempt to account for the errors. The latter approach is particularly troublesome, as accidental delivery of radiation to sensitive tissues obviously cannot be undone.

In view of the foregoing, what is needed is a system to efficiently identify potential delivery errors. It is further desirable to identify such errors during radiation treatment so that treatment may be suspended and/or modified.

SUMMARY

To address at least the foregoing, some embodiments provide a system, method, apparatus, and means to deliver treatment radiation to a target, acquire an image representing the treatment radiation during delivery of the treatment radiation, determine a position of a leaf of a collimator during delivery of the treatment radiation based on the image, and present a notification of an error during delivery of the treatment radiation based on the determined position. According to some aspects, delivery of the treatment radiation is suspended based on the determined position.

In further aspects, the image is rotated based on a rotation of the collimator specified by a treatment plan, and it is determined whether the collimator conforms to the specified rotation based on the rotated image. Determination of the leaf position, according to some aspects, may include determination of an image intensity profile representing an area of the image associated with the leaf, determination of a second derivative of the image intensity profile, and determination of the position of the leaf based on a zero crossing of the determined second derivative.

Some aspects may include identification of each of a plurality of pixels of the image as a shadow pixel or an exposed pixel based on a treatment plan, and determination of a plurality of the plurality of pixels which are incorrectly identified as a shadow pixel or an exposed pixel based on a threshold pixel value. Aspects may also or alternatively include identification of a first area of the image associated with the leaf, identification of a second area of the image associated with a second leaf opposing the first leaf, and comparison of a statistical distribution of pixel values of the first area with a statistical distribution of pixel values of the second area.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated by the inventor for carrying out the described embodiments. Various modifications, however, will remain readily apparent to those in the art.

Figure 1:
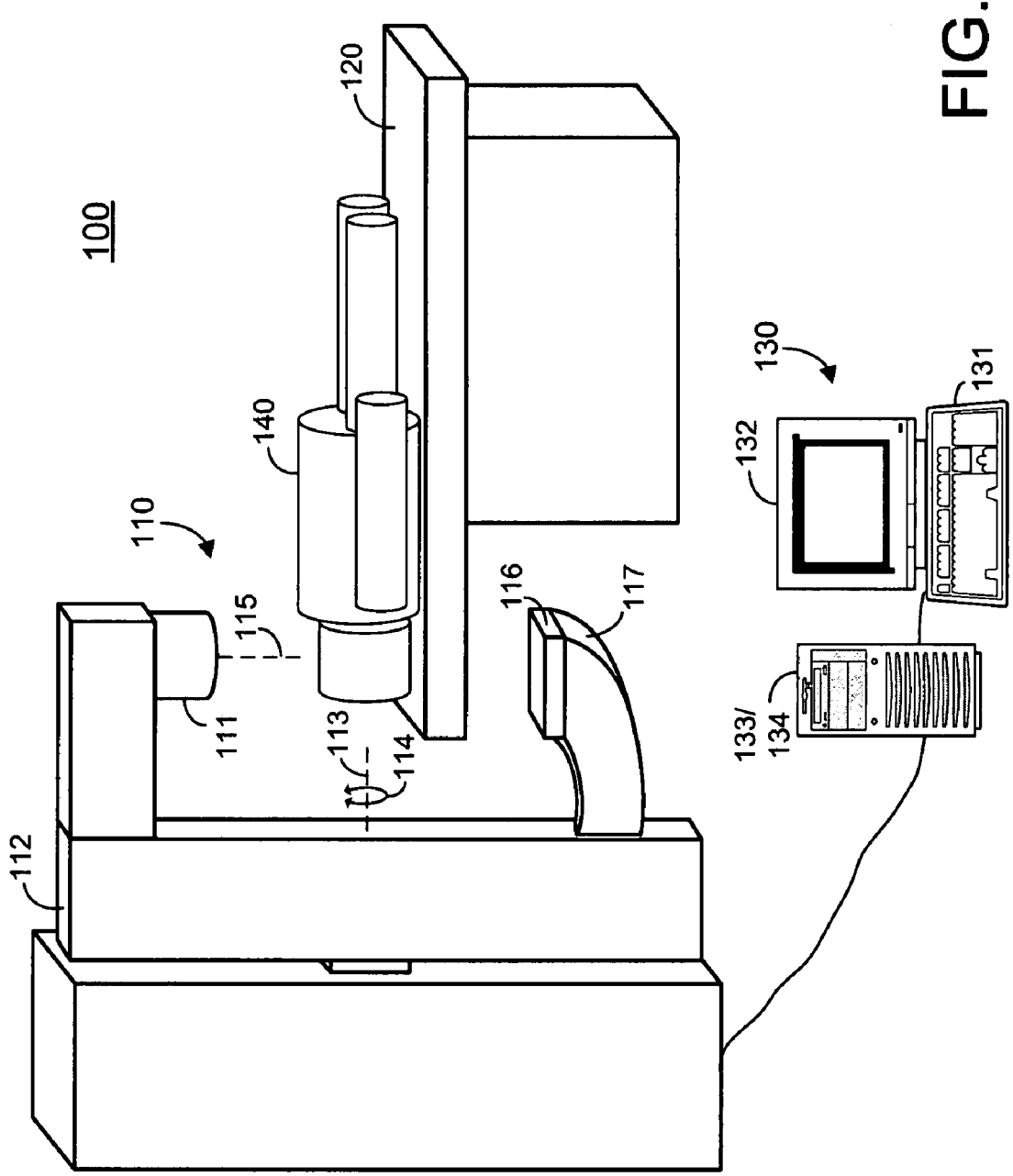
FIG. 1 is a perspective view of a radiation treatment room according to some embodiments.

FIG. 1 illustrates radiation treatment room 100 pursuant to some embodiments. Radiation treatment room 100 includes linear accelerator (linac) 110, table 120 and operator console 130. The elements of radiation treatment room 100 may be used to deliver radiation to a target volume of beam object 140. In this regard, beam object 140 may comprise a patient positioned to receive radiation according to a radiation treatment plan. The elements of treatment room 100 may be employed in other applications according to some embodiments.

Linac 110 generates and emits the radiation, and is primarily composed of treatment head 111 and gantry 112. Treatment head 11 includes a beam-emitting device (not shown) for emitting a radiation beam used during calibration, verification, and/or treatment. The radiation beam may comprise electron, photon or any other type of radiation. According to some embodiments, the radiation beam exhibits energies in the megavoltage range (i.e. >1 MeV) and may therefore be referred to as megavoltage radiation.

Also included within treatment head 111 is a beam-shielding device, or collimator, for shaping the beam and for shielding sensitive surfaces from the beam. The collimator may be rotated and various elements of the collimator may be positioned according to a treatment plan. Details of treatment head 111 according to some embodiments will be described below with respect to FIG. 2.

Treatment head 111 is coupled to a projection of gantry 112. Gantry 112 is rotatable around gantry axis 113 before, during and after radiation treatment. As indicated by arrow 114, gantry 112 may rotate clockwise or counter-clockwise according to some embodiments. Rotation of gantry 112 serves to rotate treatment head 111 around axis 113.

During radiation treatment, a radiation beam is emitted from treatment head 111 as a divergent beam. The beam is emitted towards an isocenter of linac 110. The isocenter is located at the intersection of beam axis 115 and gantry axis 113. Due to divergence of the radiation beam and the shaping of the beam by the aforementioned beam-shaping devices, the beam may deliver radiation to a volume of beam object 140 rather than only to the isocenter.

Table 120 supports beam object 140 during radiation treatment. Table 120 may be adjustable to assist in positioning a treatment area of beam object 140 at the isocenter of linac 110. Table 120 may also be used to support devices used for such positioning, for calibration and/or for verification.

Imaging device 116 may acquire images before, during and/or after radiation treatment. For example, imaging device 116 may be used to acquire images for verification and recordation of a target volume position and of an internal patient portal to which radiation is delivered. According to some embodiments, an imaging device is additionally or alternatively located between treatment head 111 and object 140. Such an imaging device may acquire an image representing radiation emitted from treatment head 111 before the radiation is attenuated by beam object 140.

Imaging device 116 may be attached to gantry 112 in any manner, including via extendible and retractable housing 117. Rotation of gantry 112 may cause treatment head 111 and imaging device 116 to rotate around the isocenter such that isocenter remains located between treatment head 111 and imaging device 116 during the rotation.

Imaging device 116 may comprise any system to acquire an image based on received megavoltage photon radiation. In a case that linac 110 is capable of producing kilovoltage photon radiation via beamline modification or other techniques, imaging device 116 may also acquire images based on such kilovoltage radiation. In some embodiments, imaging device 116 is a flat-panel imaging device using a scintillator layer and solid-state amorphous silicon photodiodes deployed in a two-dimensional array. In operation, the scintillator layer receives photons and generates light in proportion to the intensity of the received photons. The array of photodiodes receives the light and records the intensity of received light as stored electrical charge.

In other embodiments, imaging device 116 converts received photons to electrical charge without requiring a scintillator layer. The photons are absorbed directly by an array of amorphous selenium photoconductors. The photoconductors convert the photons directly to stored electrical charge. Imaging device 116 may also comprise a CCD or tube-based camera. Such an imaging device may include a light-proof housing within which are disposed a scintillator, a mirror, and a camera.

The charge developed and stored by imaging device 116 represents radiation intensities at each location of a radiation field produced by a beam emitted from treatment head 111. Since object 140 is located between treatment head and imaging device 116, the radiation intensity at a particular location represents the attenuative properties of tissues along a divergent line between a radiation source in treatment head 111 and the particular location. The set of radiation intensities acquired by imaging device 116 may therefore comprise a two-dimensional projection image of these tissues.

Operator console 130 includes input device 131 for receiving instructions from an operator and output device 132, which may be a monitor for presenting operational parameters of linac 110 and imaging device 116, interfaces for receiving operator instructions, and/or operator alerts. According to some embodiments, output device 132 may present an alert notifying an operator of an error during treatment delivery.

Input device 131 and output device 132 are coupled to processor 133 and storage 134. Processor 133 may execute program code to perform any of the determinations and generations described herein, and/or to cause linac 110 to perform any of the process steps described herein.

Storage 134 may also store program code to generate and/or modify a treatment plan according to some embodiments. Such code may comprise the COHERENCE™ workspace or the KONRAD™ treatment planning system sold by Siemens Medical Solutions. Accordingly, storage 134 may also store radiation treatment plans in accordance with any currently- or hereafter-known format. The treatment plans may comprise scripts that are automatically executable by elements of room 100 to provide radiation therapy fractions. Each fraction of each treatment plan may require a patient to be positioned in a particular manner with respect to treatment head 111.

Operator console 130 may be in a room other than treatment room 100, in order to protect its operator from radiation. For example, treatment room 100 may be heavily shielded, such as a concrete vault, to shield the operator from radiation generated by linac 110.

Figure 4:
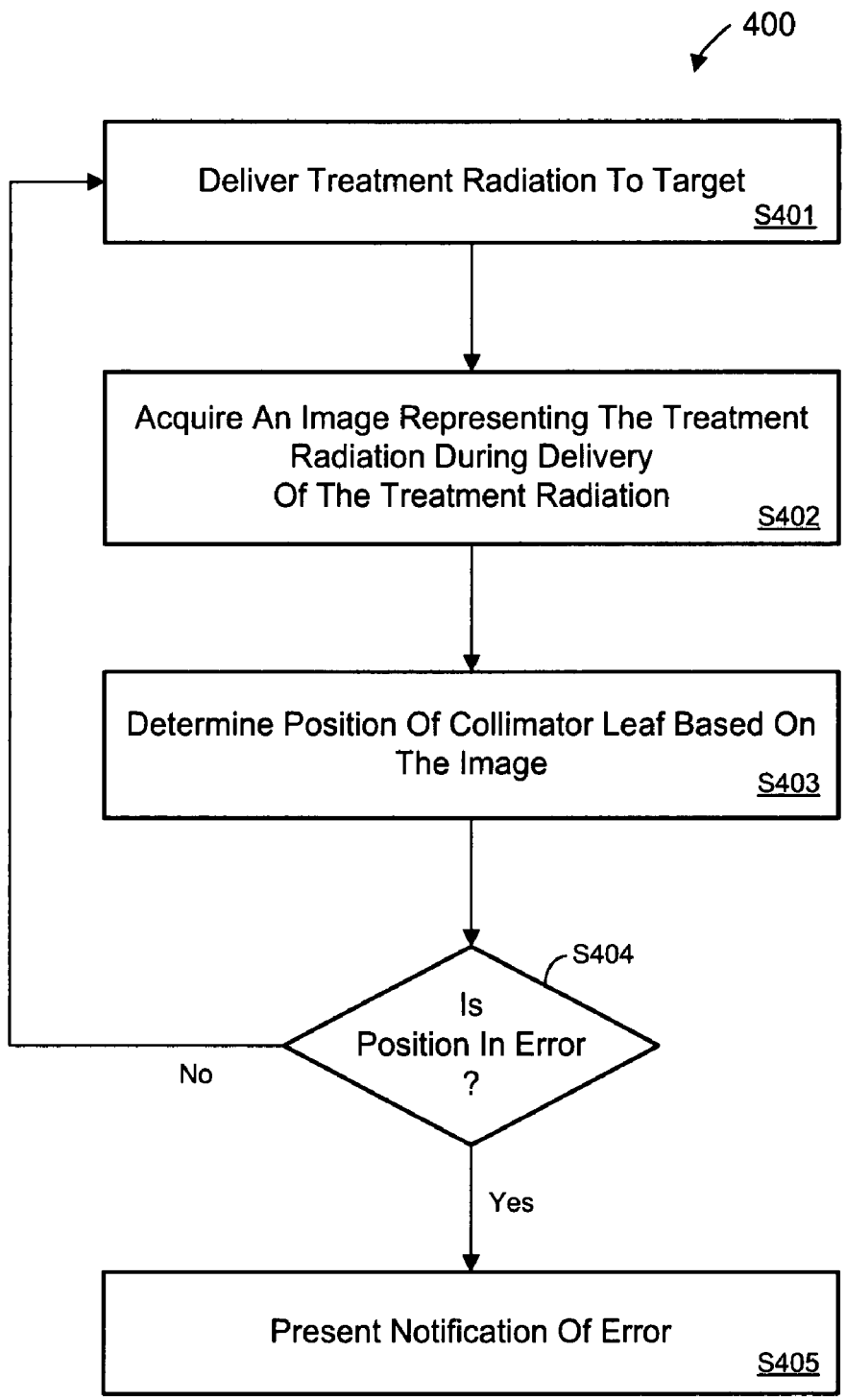
FIG. 4 comprises a flow diagram illustrating process steps according to some embodiments.
Figure 5A:
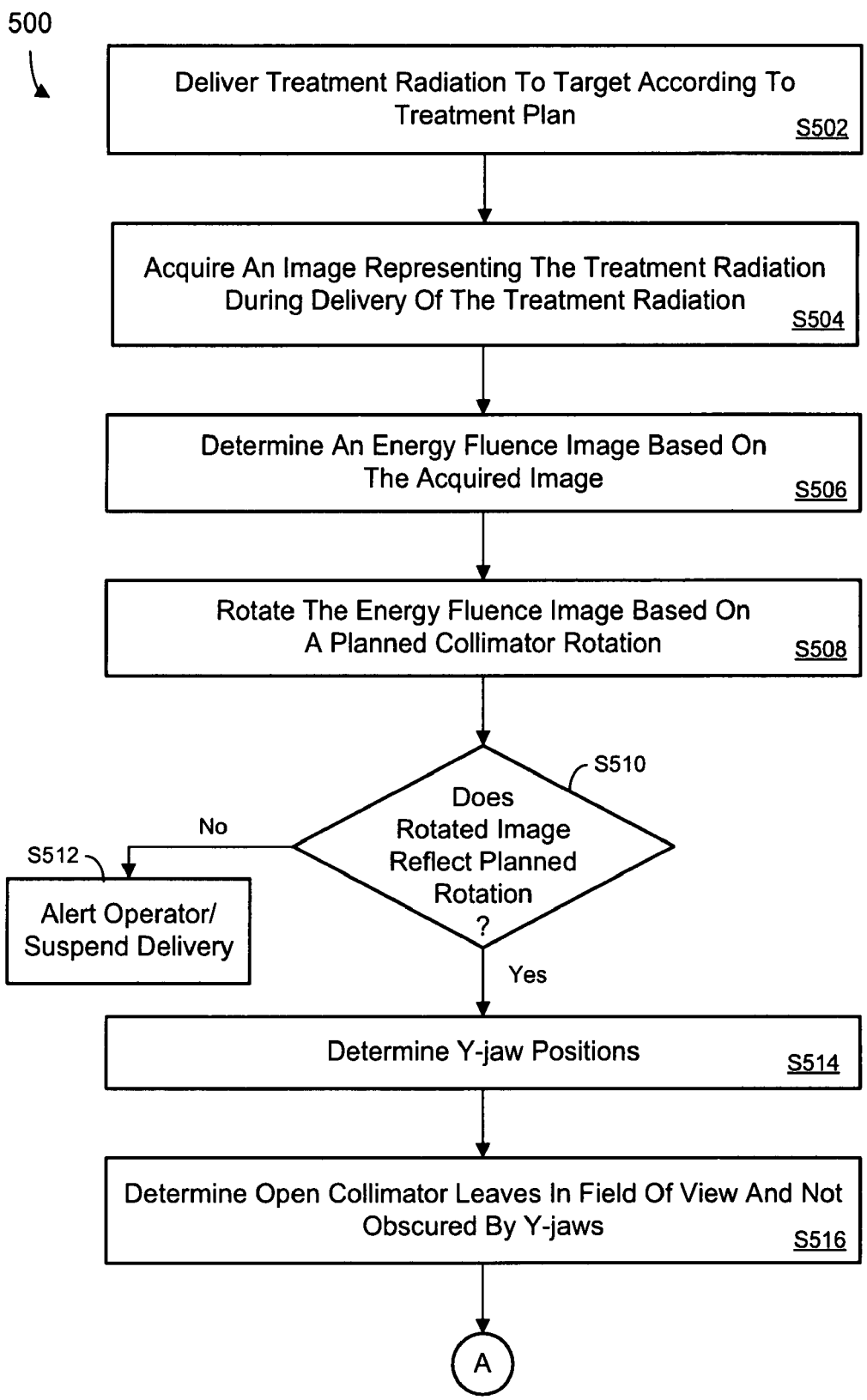
FIGS. 5A through 5C comprise a flow diagram illustrating process steps according to some embodiments.
Figure 5B:
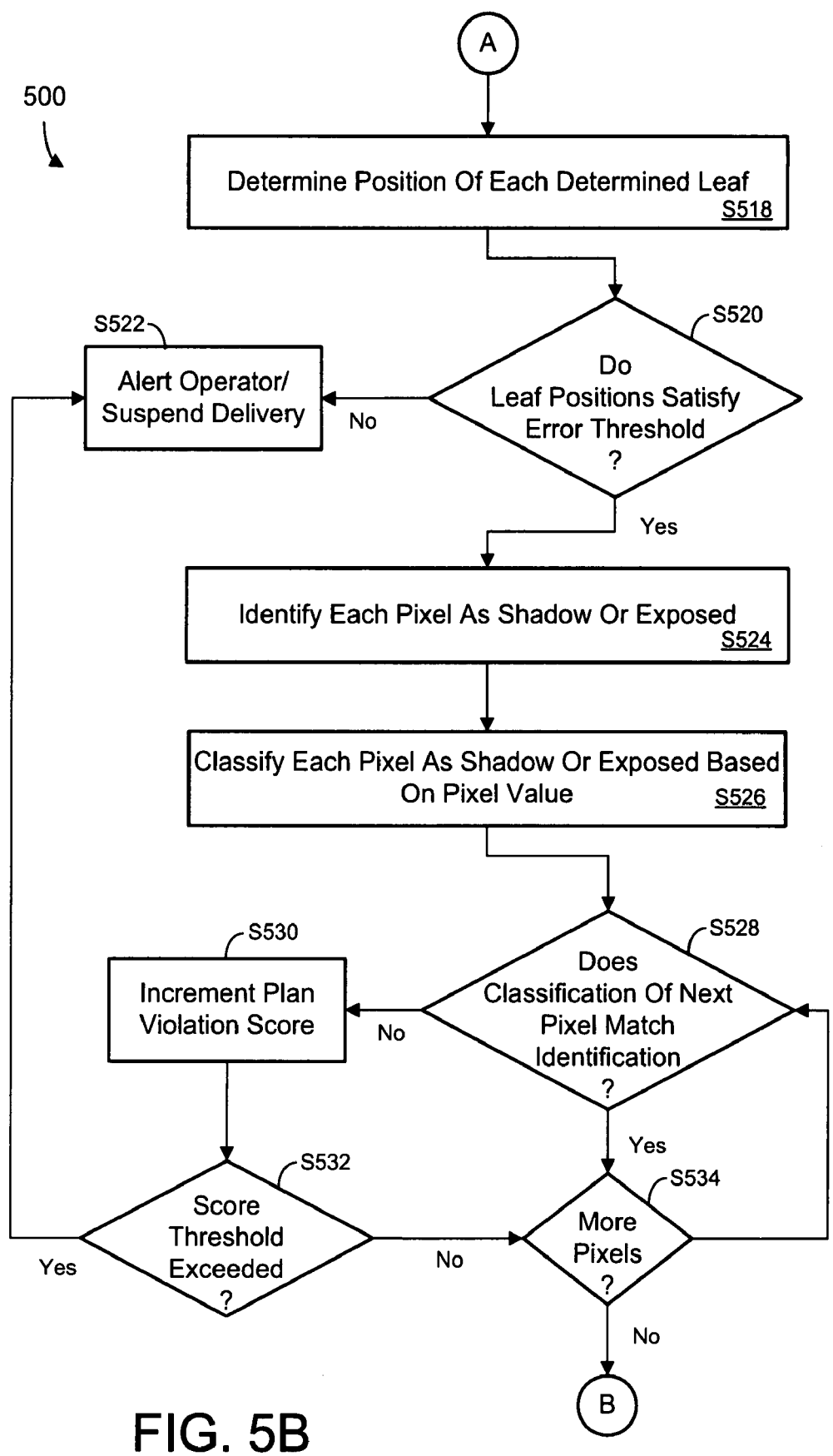
Figure 5C:
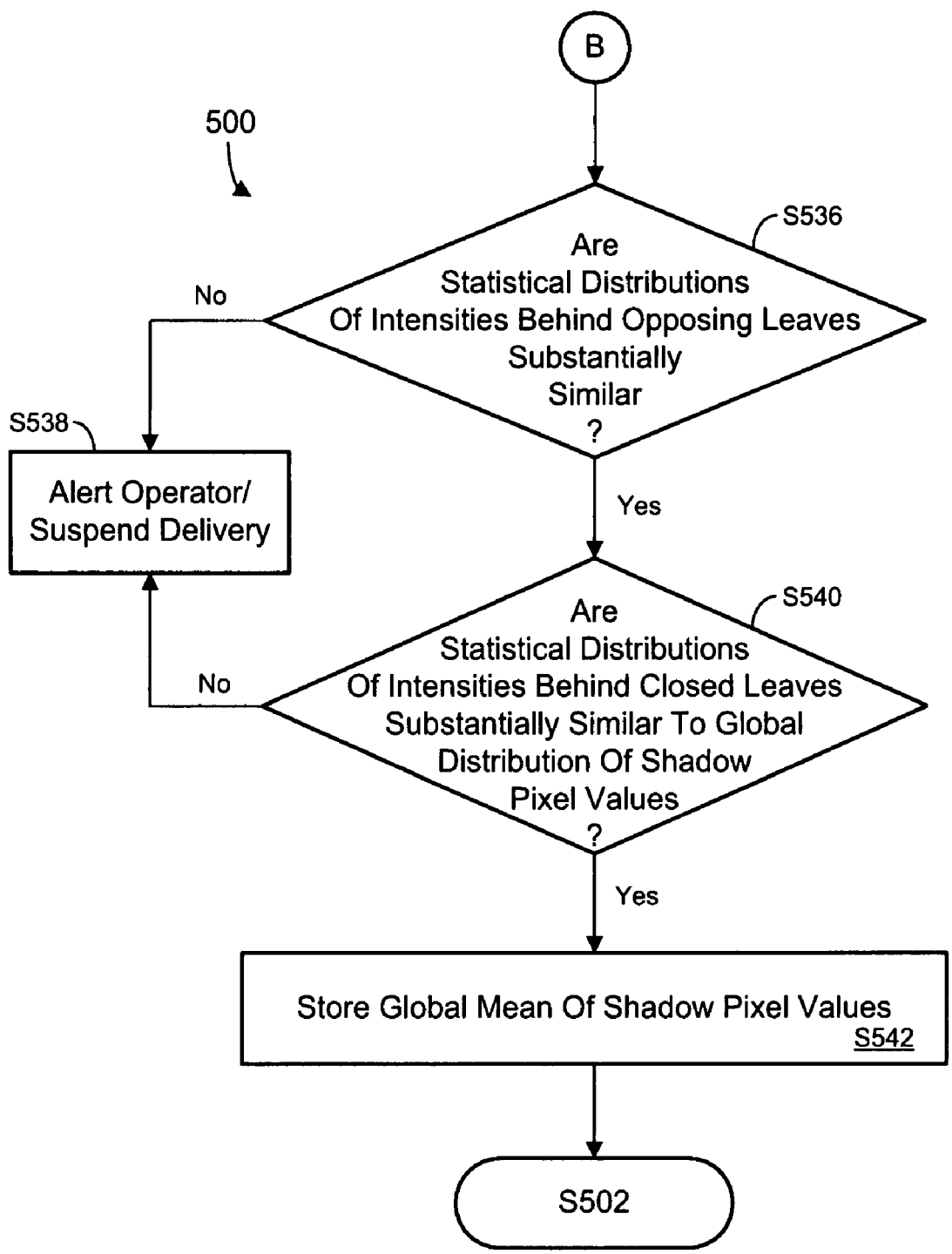

FIG. 4 illustrates treatment head 111 according to some embodiments. Treatment head 111 includes collimator 200 that may be used to conform a radiation beam to a target shape. Collimator 200 includes the pair of jaws (Y-jaws) 210 and 220 generally disposed parallel to axis y, and the pair of jaws (X-jaws) 230 and 240 generally disposed parallel to axis x. X-jaws 230, 240 are located between Y-jaws 210, 220 and object 140. The positioning of X-jaws 230, 240 and Y-jaws 210, 220 determines a size and shape of an opening through which a radiation beam may pass along axis 115.

Each of X-jaws 230, 240 and Y-jaws 210, 220 are formed of radiation attenuating material. In one embodiment, the jaws are formed of material that has x-ray transmission characteristics of less than 1%, including but not limited to tungsten.

According to some embodiments, Y-jaws 210, 220 may be independently moved toward and away from one another, and X-jaws 230, 240 may also be independently moved toward and away from one another. Also, in some embodiments, X-jaws 230, 240 and Y-jaws 210, 220 are independently rotatable about axis 115.

Figure 2:
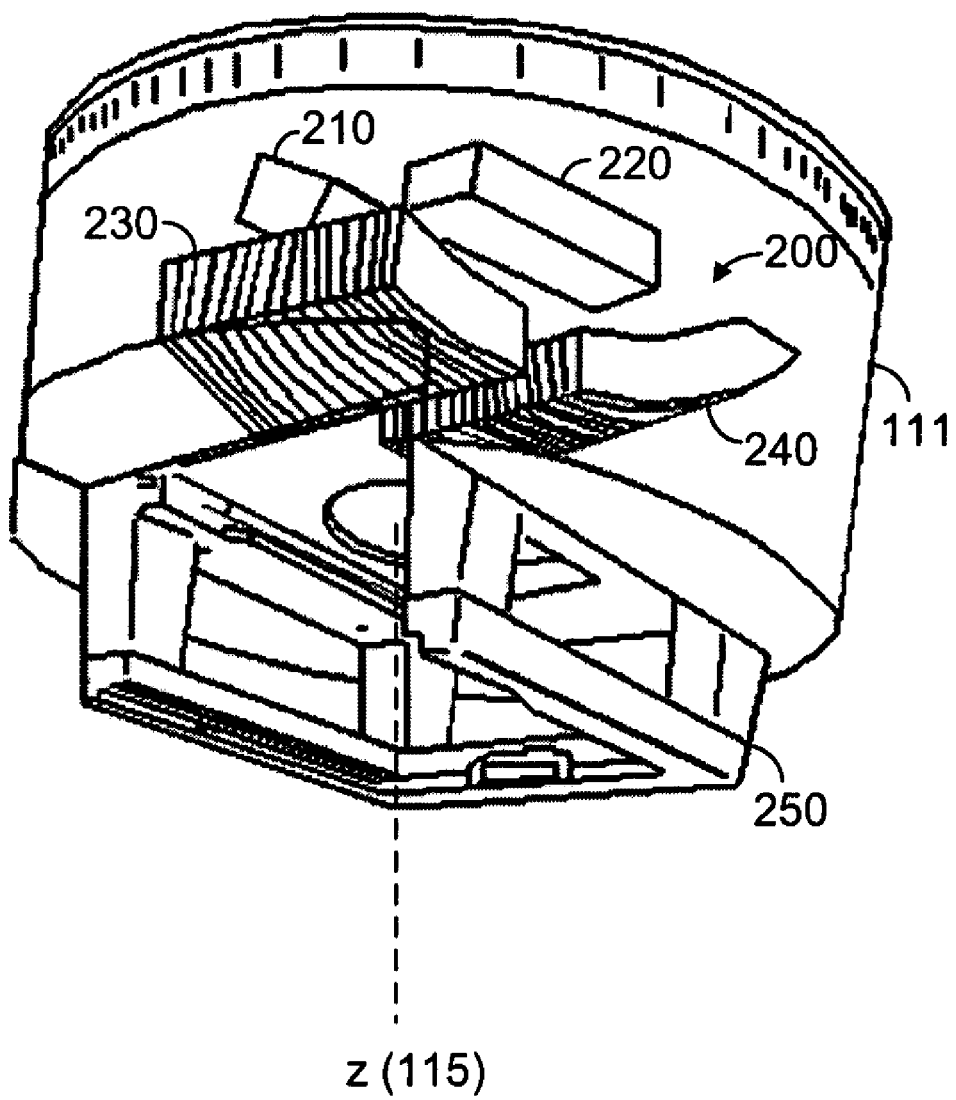
FIG. 2 is a perspective transparent view of a treatment head according to some embodiments.

As depicted in FIG. 2, X-jaws 230, 240 may be formed of a plurality of individual elements, or leaves. Each of these leaves may be independently movable along a path intersecting axis 115. Movement of each leaf may be individually controlled according to a treatment plan in order to direct a particularly-shaped beam at a target.

Treatment head 111 also includes accessory tray 250. Accessory tray 250 may be configured to receive and securely hold attachments used during the course of treatment planning and treatment (such as, for example, reticles, wedges, or the like). According to some embodiments, treatment head 111 is rotatable to rotate collimator 200 and accessory tray 250 around axis 115 while maintaining the existing physical relationships between X-jaws 210, 220 and Y-jaws 230, 240, and accessory tray 250.

Figure 3:
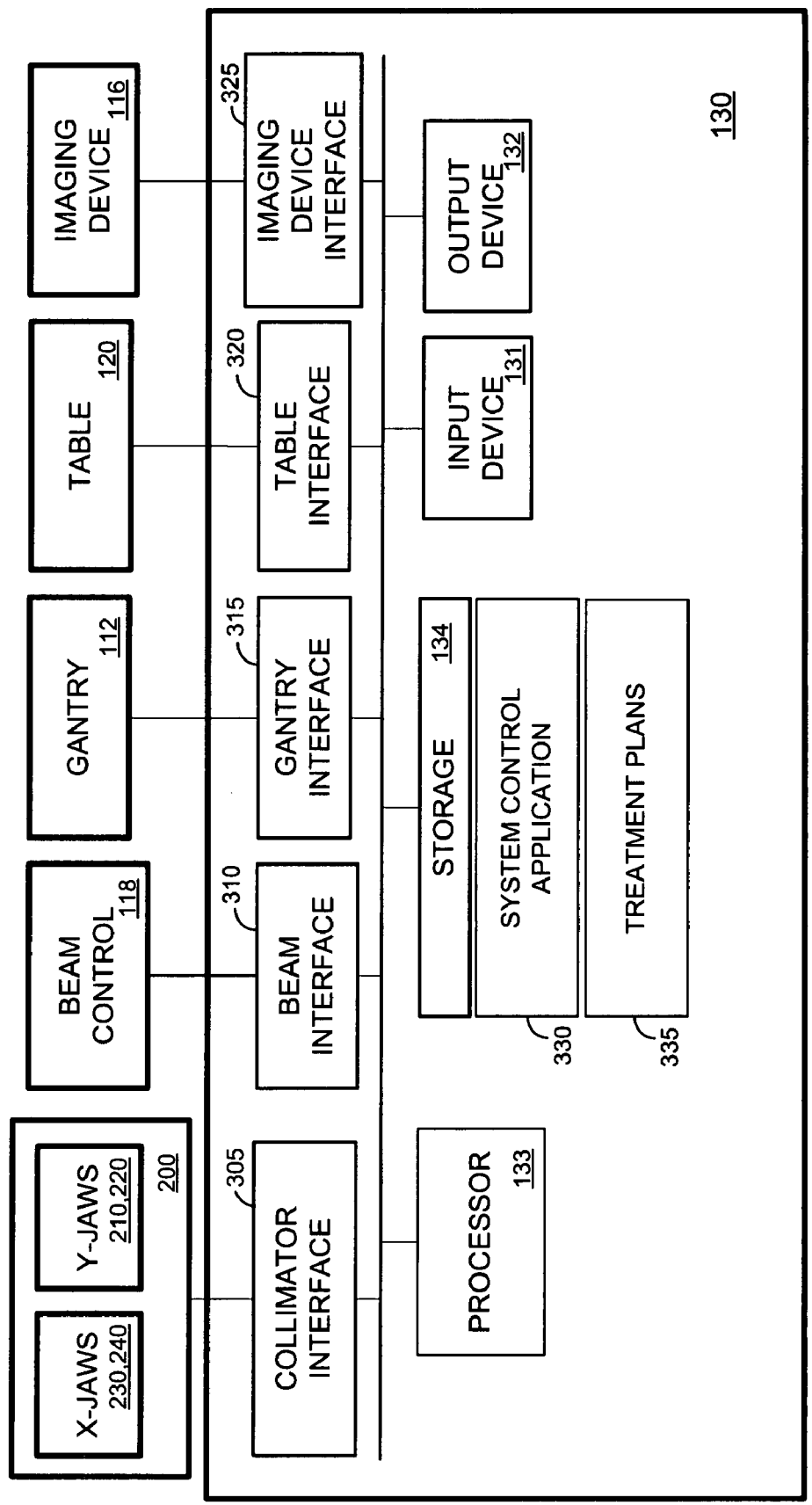
FIG. 3 is a block diagram of the internal architecture of radiation treatment room devices according to some embodiments.

FIG. 3 is a block diagram of elements of treatment room 100 according to some embodiments. As shown, operator console 130 includes several elements for interfacing with other elements of treatment room 100. Specifically, operator console 130 includes collimator interface 305, beam interface 310, gantry interface 315, table interface 320, and imaging device interface 325. Operator console 130 may be implemented by one or more separate computing systems.

Collimator interface 305 may be used to control the opening and closing of each of jaws 210 through 240, the independent rotation of each pair of jaws, and/or the rotation of collimator 200. As described above, this control may be based on parameters specified by a radiation treatment plan.

Beam interface 310 may control beam-generating elements of linac 110 based on desired beam characteristics. In particular, beam interface 310 may controls signals to generate a radiation beam having particular radiation energy.

Interfaces 315 through 325 may comprise dedicated hardware and/or software interfaces, and one or more of interfaces 315 through 325 may reside in processor 133. One or more of interfaces 315 through 325 may be implemented by a single interface. For example, interfaces 305 through 310 may be implemented by a single Ethernet interface and interfaces 315 and 325 may be implemented by proprietary interfaces for interfacing with table 120 and imaging device 116.

Operator console 130 also includes processor 133 and storage 134. Processor 133 may execute processor-executable program code stored in storage 134 to provide some or all of the functionality described herein. In this regard, storage 134 stores processor-executable process steps of system control application 333.

System control application 330 may comprise processor-executable program code to implement process steps described herein. System control application 330 may also comprise program code to generate and/or modify a treatment plan according to some embodiments. In this regard, system control application 330 may comprise the COHERENCE™ workspace or the KONRAD™ treatment planning system sold by Siemens Medical Solutions.

Storage may also store treatment plans 335 in accordance with any currently- or hereafter-known format. Treatment plans 335 may comprise scripts that are automatically executable by linac 110 and treatment table 140 to provide radiation therapy fractions. Each of treatment plans 335 may require a patient to be positioned in a particular manner with respect to treatment head 111, collimator 200 to be rotated to a particular degree, and each element of jaws 210 through 240 to be positioned in a particular manner.

A hardware environment according to some embodiments may include less or more elements than those shown in FIGS. 1 through 3. In addition, embodiments are not limited to the devices and/or to the illustrated environment.

FIG. 4 is a flow diagram of a process according to some embodiments. Process 400 and the other processes described herein may be performed using any suitable combination of hardware, software or manual means. Software embodying these processes may be stored by any medium, including a fixed disk, a floppy disk, a CD-ROM, a DVD-ROM, a Zip™ disk, a magnetic tape, or a signal. Examples of these processes will be described below with respect to the elements of treatment room 100, but embodiments are not limited thereto.

Process 400 may be performed after a patient has been placed on a treatment table and is awaiting treatment. In some embodiments, process 400 is preceded by acquisition of correction images for performing corrections on images acquired by imaging device 116. These corrections may comprise offset correction to account for dark current effects, gain correction to account for variations in pixel sensitivity, and dead pixel correction to account for malfunctioning pixels.

Initially, treatment radiation is delivered to a target at S401. The treatment radiation may be delivered in accordance with a pre-established radiation treatment plan. According to some embodiments of S401, gantry 112 may be rotated to a position specified by a treatment plan, collimator 200 may be rotated according to the treatment plan, and jaws 210 through 240 may be positioned according to the treatment plan. Beam control 118 then operates to cause linac 110 to generate a radiation beam having an energy and characteristics specified by the treatment plan.

Next, at S402, an image is acquired representing the treatment radiation. The image is acquired during delivery of the treatment radiation. For purposes of the present example, it will be assumed that the image is acquired at S402 by an imaging device located between treatment head 111 and beam object 140. Accordingly, the acquired image is a two-dimensional representation of the energy fluence entering beam object 140. Each pixel of the acquired image represents the radiation intensity at a corresponding location of the energy fluence. Some embodiments will be described below in which the acquired image is a portal image acquired by imaging device 116.

A position of a collimator leaf is determined based on the acquired image at S403. The position of the collimator leaf is determined in some embodiments by obtaining an x-coordinate associated with the leaf and identifying a y-coordinate at which the image transitions from light to shadow. Detailed examples of such a determination according to some embodiments are provided below. Some embodiments of S403 comprise determining the position of jaws 210, 220 (i.e., in terms of x-coordinates) and the position of each leaf of jaws 230, 240.

At S404, it is determined whether the determined position is in error. The determined position is compared with a position of the leaf specified by the treatment plan in some embodiments of S404. Some embodiments of S404 compare all the positions of the jaws and leaves determined at S403 with their respective planned positions, and determine an error based on whether the comparison indicates an acceptable level of disparity between the determined positions and the planned positions.

Flow returns to S401 and continues as described above if the position is determined to not be in error at S404. Accordingly, treatment radiation continues to be delivered according to a treatment plan and the position of the collimator leaf is periodically verified until the treatment plan is completed. If the determination at S404 is positive, a notification of the error is presented at S405.

Notification of the error may include displaying an error message on output device 132. The error message may include details of the positioning error, and/or may display the image acquired at S402 with annotations indicating the incorrectly-positioned leaf. S405 may further include suspending delivery of the treatment radiation and waiting for operator intervention.

Process 500 may also be executed by any suitable combination of hardware and software. Some embodiments of process 500 include process 400 of FIG. 4, but embodiments are not limited thereto.

As described with respect to process 400, process 500 may be preceded any suitable quality assurance procedures. A treatment plan is also established prior to process 500. Treatment radiation is delivered to a target at S502 according to the treatment plan. Delivery of the radiation at S502 may proceed in some embodiments as described in conjunction with S401.

An image representing the treatment radiation is acquired during delivery of the treatment radiation at S504. The acquired image may comprise a portal image acquired by imaging device 116. Due to the position of imaging device 116 shown in FIG. 1, the portal image represents radiation that was emitted from treatment head 111 and subsequently attenuated by matter disposed between treatment head 111 and device 116.

Figure 6:
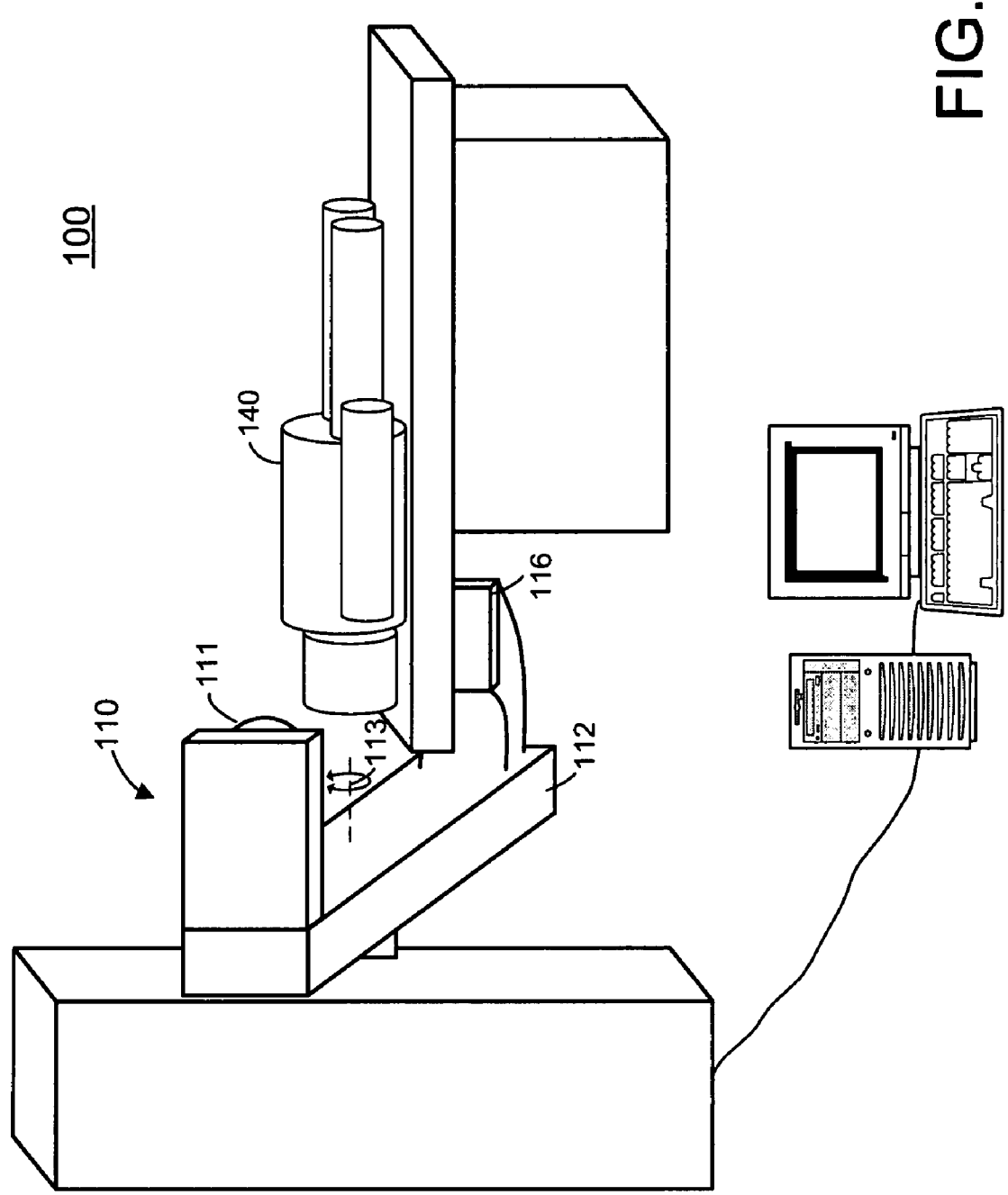
FIG. 6 is a perspective view of a radiation treatment room according to some embodiments.

Gantry 112 need not be in the position depicted in FIG. 1 during embodiments of S502 and S504. As mentioned above, gantry 112 may be rotated to an angle specified by the treatment plan. FIG. 6 is a perspective view of treatment room 100 according to some embodiments. Gantry 112 is shown rotated around axis 113 from the position of FIG. 1. However, object 140 remains between treatment head 111 and imaging device 116 so as to deliver treatment radiation to and acquire an image of object 140.

An energy fluence image is determined at S506 based on the acquired image. No additional processing is necessary at S506 if the acquired image is itself an energy fluence image as described with respect to process 400. In a case that the acquired image is a portal image, the energy fluence image may be determined therefrom using any suitable known techniques.

According to some techniques, contributions of patient scatter and beam hardening are initially removed from the portal image at S506. The resulting image is intended to represent only primary radiation (i.e., radiation that traveled directly from the beam source to imaging device 116). These contributions may be removed by using a previously-acquired and corrected cone beam CT image to determine the actual radiological thicknesses of structures shown in the acquired image, and removing artifacts that do not represent actual radiological thicknesses. Other techniques for removing contributions of patient scatter and beam hardening include registering the acquired image with a CT image used to develop the treatment plan and applying a Monte Carlo simulation to determine the contributions. Scatter estimation methods based on the superposition of scatter kernels may also be used to iteratively estimate the contributions of patient scatter and beam hardening. According to some embodiments, scatter may be measured directly within the shadows of beam-stopping elements that obscure the primary radiation from impinging fully on imaging device 116.

After correcting for scatter and beam hardening, the portal image is processed to yield a thickness image in which each pixel value is proportional to the radiological thickness of object 140 along the ray of radiation which contributes to the pixel value. The thickness image may be constructed using a map which associates pixel values with physical electron density values for a given radiation beam.

To generate such a map, a phantom is placed on table 120 and portal images thereof are acquired. The phantom includes materials having known physical electron densities (e.g., lung tissue, water, muscle, trabecular bone, dense bone). The portal images are analyzed to identify radiation intensities associated with each material. Accordingly, a mapping may be generated to associate the radiation intensities with the known physical electron densities.

Figure 7:
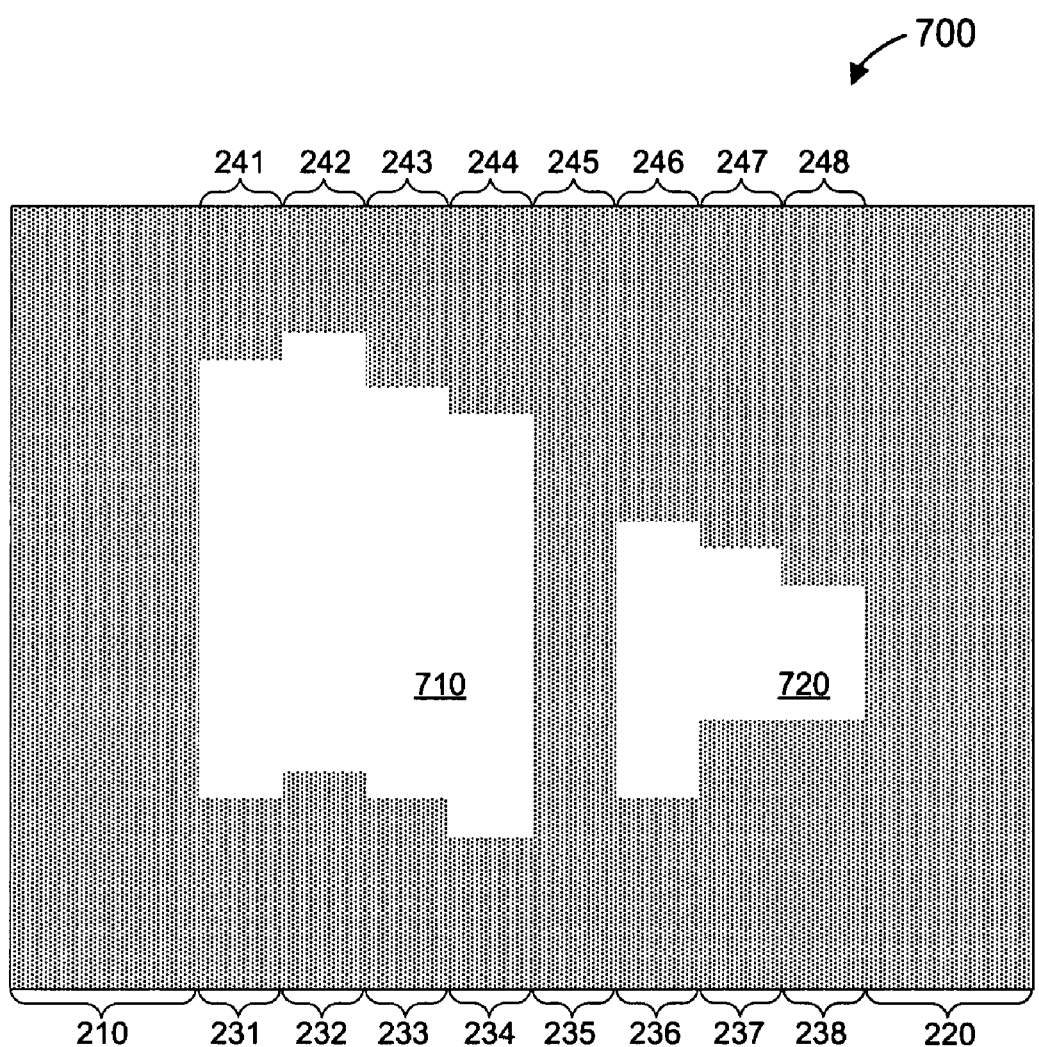
FIG. 7 depicts an energy fluence image according to some embodiments.

Next, the portal image is reverse-attenuated through the thickness image to determine the energy fluence image. The energy fluence image is a two-dimensional representation of the energy fluence entering beam object 140. FIG. 7 illustrates energy fluence image 700 according to some embodiments. Image 700 includes shadow areas representing portions of a radiation beam blocked by jaws 210, 220, leaves 231-238 of jaw 230, and leaves 241-248 of jaw 240. Image 700 also includes exposed areas 710 and 720 representing portions of a radiation beam which were substantially unimpeded during travel from treatment head 11 to object 140.

The energy fluence image is rotated at S508 based on a planned collimator rotation. According to some embodiments, the planned collimator rotation is acquired from the current treatment plan of treatment plans 335. The energy fluence image is then rotated to simulate an image that would have been obtained had the collimator been set at zero degrees or another reference position. For example, image 700 of FIG. 7 represents a zero degree collimator rotation.

At S510, it is determined whether the rotated image reflects the planned collimator rotation. According to some embodiments of S510, an edge detection algorithm is applied to the rotated image, followed by a transform such as the Hough transform. Next, the output of the transform is analyzed to verify that the peak values occur along the x- and y-axes (i.e., 0 and 90 degrees). Alternatively, the Radon transform may be used to map lines in the image to points. The position of these points in Radon transform space yields the orientations of the axes.

If the rotated image does not reflect the planned rotation (e.g., the peak values occur at unacceptable locations), flow proceeds to S512 to alert an operator and to suspend delivery of the treatment radiation. The alert may comprise an error message displayed on output device 132 and/or an audible signal. Flow proceeds from S510 to S514 if it is determined at S510 that the rotated image reflects the planned rotation.

Figure 8A:
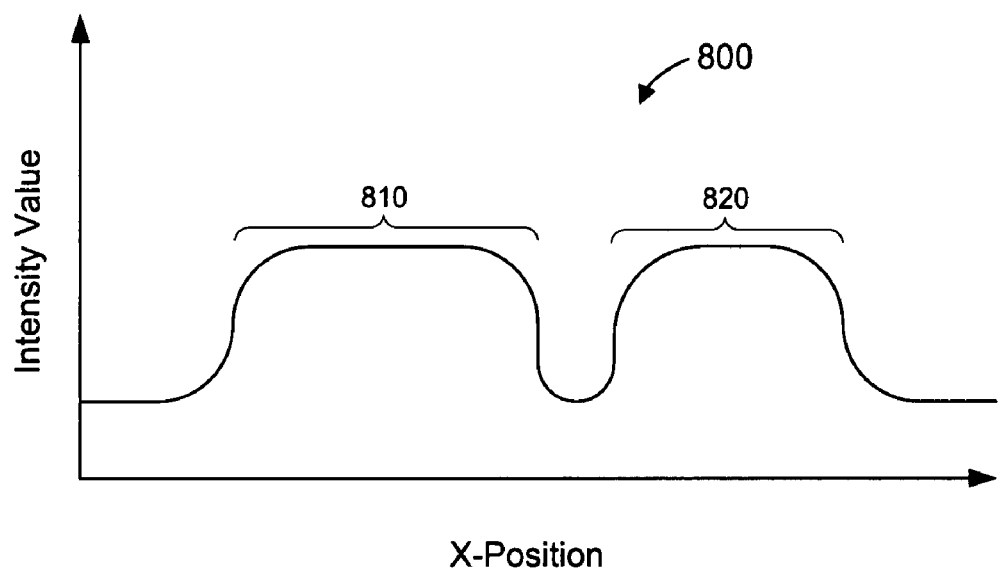
FIGS. 8A and 8B illustrate determination of a jaw position according to some embodiments.

The position of the Y-jaws is verified at S514. In some embodiments of S514, Y-jaws 210, 220 are assumed to travel along the x-axis of image 700. A value of image 700 is determined for each x-position of image 700. To account for noise or other artifacts, the value may be determined from a rank-order criterion such as the $90^{th}$ percentile rank of pixel values. FIG. 8A depicts graph 800 of the determined intensities for each x-position of image 700. For example, portion 810 corresponds to area 710 of image 700 and portion 820 corresponds to area 720.

Figure 8B:
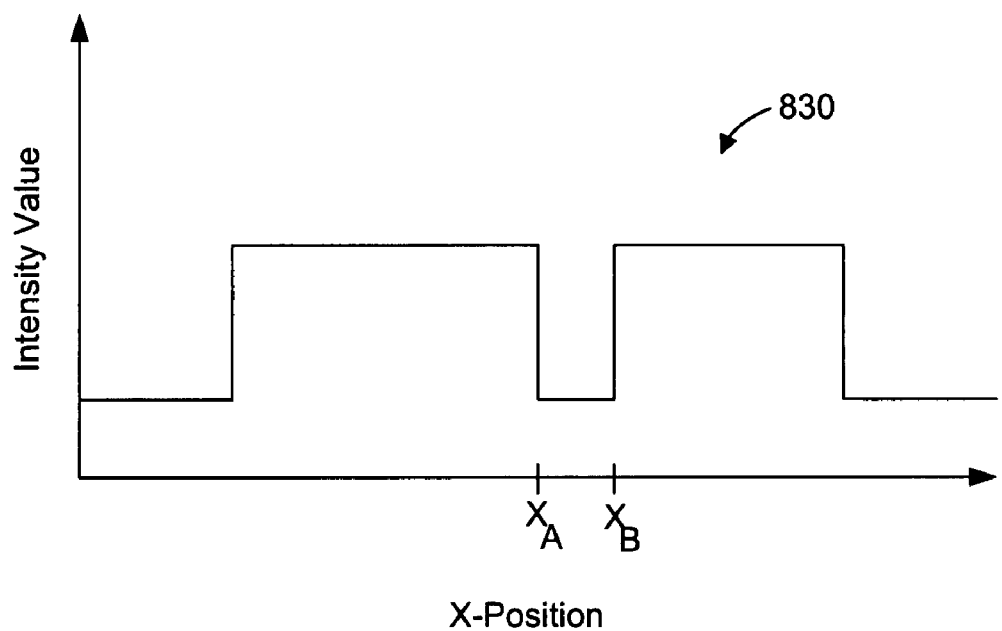

The series of determined values may be smoothed with a low pass filter to reduce penumbra effects. Graph 830 of FIG. 8B shows the results of smoothing graph 800 according to some embodiments. The second derivative of the smoothed series is calculated, and, based on the treatment plan, search windows are defined which are centered at the planned positions of Y-jaws 210, 220. The Y-jaws are determined to be located at the zero crossings within the search windows. By searching only within these search windows, process 500 avoids incorrectly identifying zero crossings at positions $X_A$ and $X_B$.

Next, at S516, a set of collimator leaves is determined. The set includes those collimator leaves which are open (i.e., not touching a corresponding opposing leaf), which are in the field of view of the energy fluence image, and not obscured by the Y-jaws. The determination at S516 may be based on the positions of the leaves specified by the treatment plan and the Y-jaw positions determined at S514. In the example of FIG. 7, leaves 231-234, 236-238, 241-244, and 246-248 are determined at S516.

The position of each determined leaf is then determined at S518. The determination of leaf position may proceed similarly to the determination of jaw position described at S514, albeit with respect to y-position. The determined leaf positions may be displayed in conjunction with the planned leaf positions on output device 132.

At S520, it is determined whether the determined leaf positions satisfy an error threshold. The error threshold may reflect a cumulative positioning error that is deemed to be acceptable. In this regard, a distance between the determined and planned positions of each leaf may be determined, all the determined distances may be summed, and the sum may be compared with an error threshold.

Flow proceeds to S522 if the positions do not satisfy an error threshold. At S522, an operator is alerted and delivery of the treatment radiation is suspended as described with respect to S512. Flow continues from S520 to S524 if the error threshold is satisfied.

Each pixel of the energy fluence image is identified at S524 as a shadow pixel or an exposed pixel. According to some embodiments, the above-determined actual positions of the collimator elements are used to determine which of the pixels of the energy fluence image should reflect low radiation intensity (i.e., shadow) and which of the pixels of the energy fluence image should reflect low radiation intensity (i.e., exposed). This determination may take into account the divergence of the radiation beam.

Figure 9:
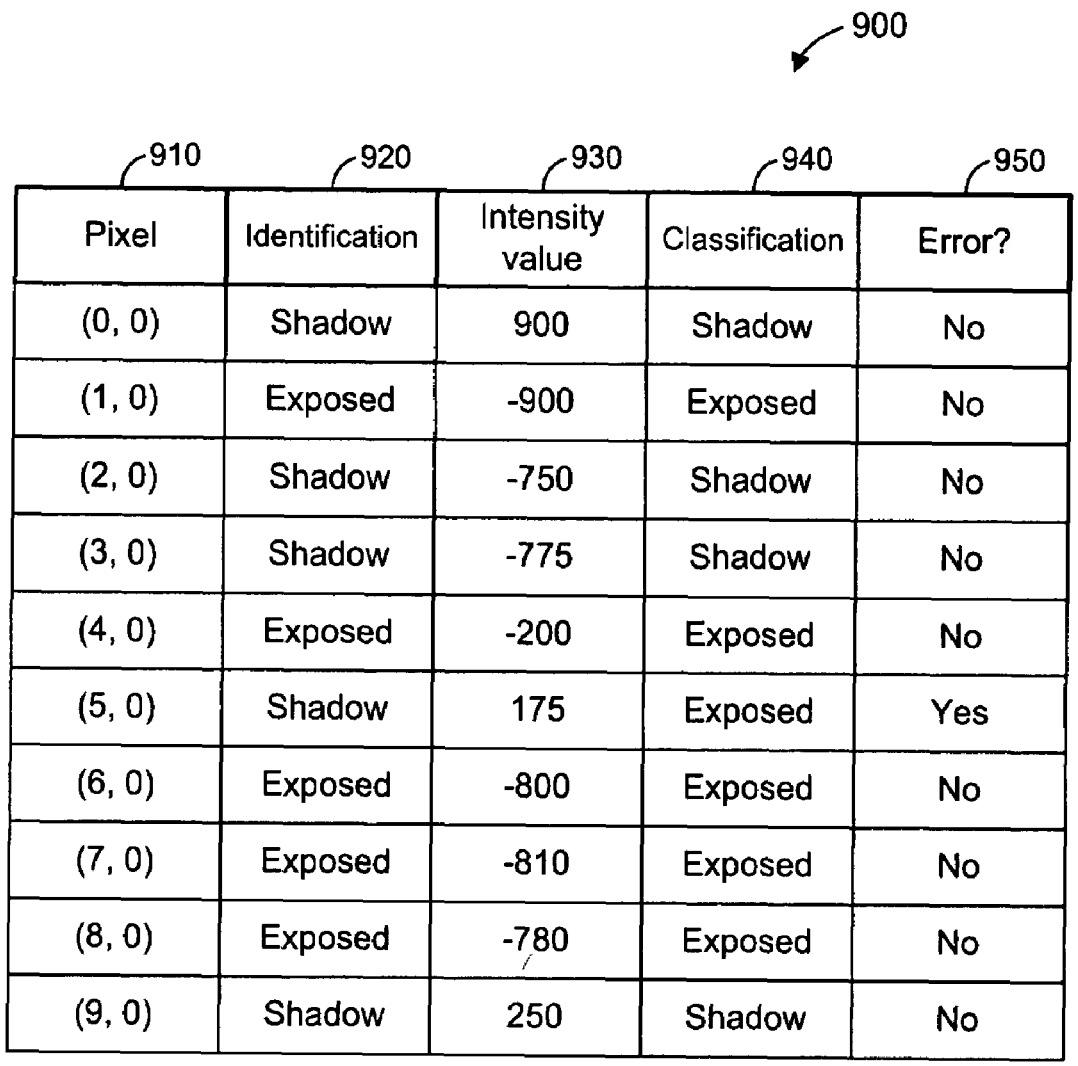
FIG. 9 is a tabular representation of data to evaluate pixel identification according to some embodiments.

FIG. 9 is a tabular representation of data 900 for describing some embodiments of S524 through S534. For example, field 910 is populated with identifiers of each pixel of the energy fluence image and field 920 associates each pixel with a "shadow" or "exposed" flag based on the identification of S524. Field 930 also specifies an intensity value of each pixel of the energy fluence image.

At S526, each pixel of the image is classified as a shadow pixel or an exposed pixel based on its respective intensity value. The intensity value of each pixel is compared with a threshold value (e.g., (avg(intensity of shadow pixels)+avg (intensity of exposed pixels))/2) to perform the classification in some embodiments. Field 940 of FIG. 9 illustrates the classification of each pixel in a case that the threshold value is 100. Field 950, in turn, indicates whether or not the identification specified in field 920 matches the classification specified in field 940 for each pixel.

The threshold of the classifier may be based on a discriminant hypersurface which has been determined by a training process. Training is achieved by presenting to a machine learning algorithm the properties of pixels in the shadow regions and exposed regions as well as corresponding labels assigning each pixel to a region. As described above, these regions and region labels are identified on the basis of the determined positions of the collimator elements. The hypersurface embodies the differences in the statistical distributions of pixels in the shadow and exposed regions.

Next, at S528, it is determined whether the classification of a pixel matches the identification of the pixel. A first row of field 950 is analyzed in some embodiments of S528. If the classification does not match the identification, a plan violation score is incremented at S530. Next, it is determined whether the score exceeds a threshold at S532. If so, flow returns to S522 to alert the operator and suspend treatment delivery.

Flow arrives at S534 if the score threshold is not exceeded, or if the determination at S528 is positive. If more pixels exist to be evaluated at S528, flow returns to S528 to evaluate a next pixel. Flow continues to S536 from S534 if every pixel has been evaluated and the score threshold has not been exceeded.

At S536, it is determined whether statistical distributions of intensities behind opposing leaves are substantially similar, as would be expected on the basis of uniformity of the radiation within a close proximity. The intensities may be obtained based on the known x-positions of each leaf and the y-positions determined at S518. Any manner of statistical distribution may be used in the comparison, including but not limited to student's t-test or a similar statistical method.

Flow proceeds to S538 if the distributions are not substantially similar, and to S540 if they are substantially similar. S538 may be performed as described with respect to S512 and S522.

It is determined at S540 whether statistical distributions of intensities behind closed leaves are substantially similar to the global distribution of shadow pixel values. The closed leaves may be identified from the treatment plan and/or from the energy fluence image. For example, leaves 235 and 245 of image 700 are considered closed. The global distribution of shadow values may be determined from the intensity values of field 930 that are associated with pixels classified as "shadow". Flow continues to S538 if the determination at S540 is negative.

A global mean of shadow pixel values is stored at S542. The global mean of shadow values may be determined from the intensity values of field 930 that are associated with pixels classified as "shadow". In some embodiments, the stored global shadow mean is compared against the global shadow mean of a future segment and an alert is generated if the mean has deviated in an unexpected manner. Flow then returns to S502 and continues as described above until delivery of the treatment radiation is complete. Process 500 is performed only once per treatment segment in some embodiments, so flow may terminate after S542 according to these embodiments.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
   delivering treatment radiation to a target;
   acquiring a portal image of the target;
   determining an image based on the portal image and on electron density values of structures represented in the portal image, the image representing the treatment radiation during delivery of the treatment radiation;
   determining a position of a leaf of a collimator during delivery of the treatment radiation based on the image; and
   presenting a notification of an error during delivery of the treatment radiation based on the determined position.

2. A method according to claim 1, further comprising:
suspending delivery of the treatment radiation based on the determined position.

3. A method according to claim 1, further comprising:
comparing the determined position with a position specified by a treatment plan; and
determining that the determined position is different from the specified position.

4. A method according to claim 1, further comprising:
rotating the image based on a rotation of the collimator specified by a treatment plan; and
determining if the collimator conforms to the specified rotation based on the rotated image.

5. A method according to claim 1, wherein determining the position of the leaf comprises:
determining an image intensity profile representing an area of the image associated with the leaf;
determining a second derivative of the image intensity profile; and
determining the position of the leaf based on zero crossing of the determined second derivative.

6. A method according to claim 1, further comprising:
determining a position of a plurality of leaves of the collimator based on the image;
comparing the determined positions of the leaves specified by a treatment plan; and
determining that a total difference between the determined positions and the specified positions exceeds a threshold value.

7. A method according to claim 1, further comprising:
identifying each of a plurality of pixels of the image as a shadow pixel or an exposed pixel based on a treatment plan; and
determining a plurality of the plurality of pixels which are incorrectly identified as a shadow pixel or an exposed pixel based on a threshold pixel value.

8. A method according to claim 7, further comprising:
determining the threshold pixel value based on pixels identified as shadow pixels.

9. A method according to claim 1, further comprising:
identifying a first area of the image associated with the leaf;
identifying a second area of the image associated with a second leaf opposing the first leaf; and
comparing a statistical distribution of pixel values of the first area with a statistical distribution of pixel values of the second area.

10. An apparatus comprising:
a linear accelerator to deliver treatment radiation to a target;
a collimator comprising a plurality of leaves, the collimator to prevent a portion of the treatment radiation from reaching the target;
an imaging device to acquire a portal image of the target;
wherein the processor determines
a processor to determine an image based on the portal image and on electron density values of structures represented in the portal image, the image representing the treatment radiation during delivery of the treatment radiation and to determine a position of a leaf of a collimator based on the image and to generate a notification of an error during delivery of the treatment radiation based on the determined position.

11. An apparatus according to claim 10, the processor further to:
suspend delivery of the treatment radiation based on the determined position.

12. An apparatus according to claim 10, the processor further to:
compare the determined position with a position specified by a treatment plan; and
determine that the determined position is different from the specified position.

13. An apparatus according to claim 10, the processor further to:
rotate the image based on a rotation of the collimator specified by a treatment plan; and
determine if the collimator conforms to the specified rotation based on the rotated image.

14. An apparatus according to claim 10, wherein determination of the position of the leaf comprises:
determining an image intensity profile representing an area of the image associated with the leaf;
determining a second derivative of the image intensity profile; and
determining the position of the leaf based on a zero crossing of the determined second derivative.

15. An apparatus according to claim 10, the processor further to:
determine a position of a plurality of leaves of the collimator based on the image;
compare the determined positions with positions of the leaves specified by a treatment plan; and
determine that a total difference between the determined positions and the specified positions exceeds a threshold value.

16. An apparatus according to claim 10, the processor further to:
identify each of a plurality of pixels of the image as a shadow pixel or an exposed pixel based on a treatment plan; and
determine a plurality of the plurality of pixels which are incorrectly identified as a shadow pixel or an exposed pixel based on a threshold pixel value.

17. An apparatus according to claim 16, the processor further to:
determine the threshold pixel value based on pixels identified as shadow pixels.

18. An apparatus according to claim 10, the processor further to:
identify a first area of the image associated with the leaf;
identify a second area of the image associated with a second leaf opposing the first leaf; and
compare a statistical distribution of pixel values of the first area with a statistical distribution of pixel values of the second area.

* * * * *